US007963938B2

(12) United States Patent
Wollmann et al.

(10) Patent No.: US 7,963,938 B2
(45) Date of Patent: Jun. 21, 2011

(54) DEVICE FOR PRODUCING MEDICINAL FOAM

(75) Inventors: Jan-Christoph Wollmann, Bad Kreuznach (DE); Dorothee Schliephake, Mainz (DE)

(73) Assignee: Chemische Fabrik Kreussler & Co. (DE)

( * ) Notice: Subject to any disclaimer, the term of this patent is extended or adjusted under 35 U.S.C. 154(b) by 1055 days.

(21) Appl. No.: 10/536,862

(22) PCT Filed: Nov. 13, 2003

(86) PCT No.: PCT/EP03/12894

§ 371 (c)(1),
(2), (4) Date: May 27, 2005

(87) PCT Pub. No.: WO2004/047969

PCT Pub. Date: Jun. 10, 2004

(65) Prior Publication Data

US 2006/0178620 A1 Aug. 10, 2006

(30) Foreign Application Priority Data

Nov. 28, 2002 (DE) .............................. 202 18 493 U

(51) Int. Cl.
*A61M 37/00* (2006.01)

(52) U.S. Cl. ............................................ 604/87; 604/91

(58) Field of Classification Search .................. 604/184, 604/82-92, 246
See application file for complete search history.

(56) References Cited

U.S. PATENT DOCUMENTS

| | | | | |
|---|---|---|---|---|
| 2,630,183 | A | 3/1953 | Foutz | 169/15 |
| 2,724,383 | A * | 11/1955 | Lockhart | 604/88 |
| 3,767,085 | A | 10/1973 | Cannon et al. | 222/82 |
| 4,014,463 | A * | 3/1977 | Hermann | 222/135 |
| 4,059,109 | A * | 11/1977 | Tischlinger | 604/88 |
| 4,538,920 | A * | 9/1985 | Drake | 366/181.5 |
| 4,743,229 | A * | 5/1988 | Chu | 604/82 |
| 5,425,580 | A | 6/1995 | Beller | 366/131 |
| 5,454,805 | A * | 10/1995 | Brony | 604/406 |
| 2002/0101785 | A1* | 8/2002 | Edwards et al. | 366/268 |
| 2004/0156915 | A1 | 8/2004 | Harman et al. | 424/600 |

FOREIGN PATENT DOCUMENTS

| | | |
|---|---|---|
| EP | 0 564 505 | 12/1991 |
| WO | WO 96/08227 | 3/1996 |
| WO | WO 02/058834 | 8/2002 |
| WO | WO2004/047969 | 6/2004 |

OTHER PUBLICATIONS

International Preliminary Report (IPER) and Written Opinion dated Jul. 6, 2007 based on International Application No. PCT/EP2005/054819.

* cited by examiner

*Primary Examiner* — Nicholas D Lucchesi
*Assistant Examiner* — Nathan R Price
(74) *Attorney, Agent, or Firm* — Ohlandt, Greeley, Ruggiero & Perle, LLP

(57) ABSTRACT

A device for producing medical foam, for example, a sclerosing agent, a diagnostic agent, a therapeutic agent, etc. The device comprises an active ingredient chamber and a gas chamber. Both chambers are respectively closed by a piston and connected to a foam generator. Both pistons are interconnected, especially by a connecting element, and can be displaced together, in order to supply the active ingredient and the gas to the foam producer.

17 Claims, 2 Drawing Sheets

DEVICE FOR PRODUCING MEDICINAL FOAM

1. FIELD OF THE INVENTION

The invention refers to a device for producing in particular reproducible medicinal foam or bubble suspension of a gaseous and a liquid medium. In particular, the invention refers to a mixing device for a reproducible preparation and administration of injectables such as sclerosing agents, diagnostic agents, therapeutic agents, homeopathic agents and autologous blood, for example.

2. DISCUSSION OF THE BACKGRUOND ART

Sclerotherapy means the planned elimination of intracutaneous, subcutaneous and/or transfascial varices and the sclerotization of subfascial vessels in case of venous anomalies by injecting a sclerosing agent. The various sclerosing agents cause damage to the endothelium of the vessels. Thereafter, a secondary vascular occlusion occurs and, in the long term, the veins are transformed into a strand of fibrous tissue, i.e. sclerosis occurs. It is the purpose of the sclerotization treatment to definitely transform the veins into a fibrous strand. This can not recanalize and, in its functional result, corresponds to the surgical procedure for removing a varice. Besides a sclerotization with liquid sclerosing agents, the sclerotization with foamed sclerosing agents becomes ever more important. The foam remains in vein for a longer period. Here, surfactant sclerosing agents, such as Polidocanol, are most often made to achieve a foamy state by pumping the agent back and forth between two pumps or by shaking, whereafter it is injected in a conventional manner. At present, there is no approved technique that would allow a reproducible preparation of a standardized foam.

Further, a plurality of preparations suited for use as ultrasonic contrast media are known, some of which contain surfactants that support the formation of micro-bubbles and stabilize these. The micro-bubbles or a foam reflecting ultrasound are the true contrast medium and are produced only immediately before being administered.

A mixing device for producing medicinal foam or for producing bubbles is known from EP 0 564 505. Here, a mixer with a helically shaped mixing element is described. The mixer is an accessory element that may be permanently connected to a syringe. When a liquid and/or gaseous medium is expelled from a second syringe, the medium reaches the mixer that contains the gas in a defined volume and nature. Here, the gaseous phase and the liquid phase are mixed along the helical mixing element. Thereby, a therapeutic and/or diagnostic foam may be produced.

The mixing device described in EP 0 564 505 is disadvantageous in that the mixer fixedly secured to the syringe can easily break off or be canted because of the long lever, in particular while moving the solution back and forth. Further, the mixer is a component that, due to the helical mixing elements arranged in the mixer, can be made as an injection molded part only with complicated injection molds.

It is the object of the present invention to provide a device with which medicinal foam can be produced from a gaseous and a liquid medium in a simple manner.

SUMMARY OF THE INVENTION

The device of the present invention comprises an active agent chamber and a gas chamber. Both chambers are closed by a respective piston. Further, the device comprises a foam producing means, in particular having one or a plurality of sieves. Both the active agent chamber and the gas chamber are indirectly or directly connected to the foam producing means. According to the invention, both pistons are arranged for displacement in the respective chamber. In particular, both pistons are connected with each other or may be connected while operating the device, so that the two pistons are displaced in common within one of the two chambers, respectively. This increases the pressure in the chambers and thus supplies or conveys the active agent and the gas towards the foam producing means or through the foam producing means. Therefore, the device of the present invention is very simple to handle since one movement moves both pistons and thus both media are pressed or transported toward the foam producing means. The medicinal foam escaping from the foam producing means only has to be collected, yet it may also be applied directly.

In the device of the present invention, it is not necessary to move a gas and a liquid or a gas and a detergent back and forth between two syringes. Therefore, it is much simpler to produce a standardized sterile foam. Further, no pressurized gas container need be provided in the device of the invention.

Preferably, both pistons are interconnected through a connecting element. Here, the connecting element is preferably designed such that one of the two chambers is opened when the connecting element is displaced. Further, the displacement of the connecting element may effect a connection of both pistons. Preferably, both pistons are connected only through the operation of the device. This is advantageous in that both chambers are completely separated from each other and may be sealed. It is particularly preferred herein to form the connecting element as a feed channel, e.g. as a hollow needle. By moving the connecting element together with one of the pistons, the connecting channel is introduced into one of both chambers. If the connecting element is designed as a hollow needle, both chambers are pierced, for example, by the hollow needle penetrating the second piston.

It is particularly preferred to provide an entrainment element on the connecting element, which may in particular be designed as a bead or a plate. This allows, when moving the connecting element towards one of both pistons closing the chambers after having, for example, pierced or opened this piston, to push the same into the corresponding chamber and to increase the pressure in the chamber, so that the medium in the chamber preferably flows into the hollow needle and through the same to the foam producing means.

Instead of displacing both pistons in common that are preferably interconnected through the connecting element, it is also possible to displace both chambers. All that is relevant is the relative movement between the chambers and the pistons.

Preferably, one of the two pistons is, in particular, rigidly connected with the foam producing means. Further, one of the two pistons may also be loosely connected with the foam producing means. Preferably, the medium flows through the piston into the foam producing means. It is further preferred that also the medium from the second chamber flows through this piston. In this preferred embodiment, both media preferably mix in the foam producing means and/or immediately before the foam producing means. It is particularly preferred to press the medium from the chamber farther away from the foam producing means through a feed channel provided in the connecting element and to supply it at least partly directly to the foam producing means. In this embodiment, the media are mixed immediately in the foam producing means. If desired, a mixing element may be provided in or before the foam mixing means in which a pre-mixing of both media is effected before these are pressed through the foam producing means. This mixing element may be a kind of sponge or sintered material, for example, serving at the same time to slow down the active agent. This improves the production of foam.

Further, it is possible to provide the foam producing means within the syringe, e.g. in the hub that also forms the Luer lock.

Preferably, a foam exit opening of the foam producing means may be connected to a foam collecting receptacle. The foam collecting receptacle may be, for example, a conventional syringe which may then be connected to the foam exit opening through a Luer lock, for example.

The device of the present invention is particularly suitable for one-way use due to its simple and economic structure made of simple parts that are preferably individually producible. Particularly because of the one-way use, the required sterility can be guaranteed. It is another advantage of the present device that the drug and the gas come into contact only immediately before being applied.

BRIEF DESCRIPTION OF THE DRAWINGS

The following is a detailed description of a preferred embodiment of the invention with reference to the accompanying drawings.

In the Figures.

DETAILED DESCRIPTION OF THE PREFERRED EMBODIMENT

Figure 1:
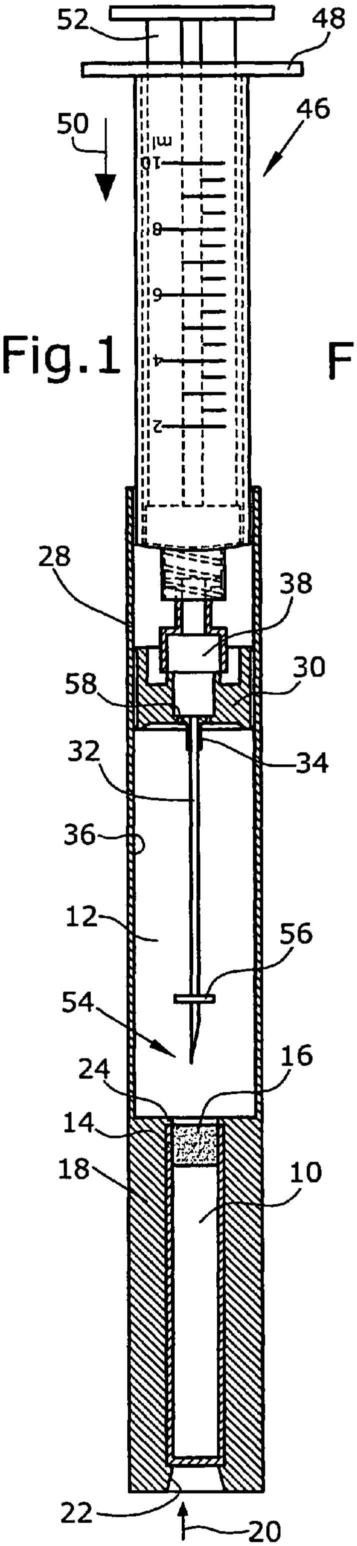
FIGS. 1-3 schematic, partly sectional side elevational views of the device in three different mixing states, and FIG. 4 a schematic exploded view of the present device.

The device of the present invention for producing medicinal foam comprises an active agent chamber 10 and a gas chamber 12. The active agent chamber 10 is designed as a carpule 14 (FIG. 4) and sealed with a first piston 16 that may be a rubber stopper or the like. The carpule 14 is held in a holder 18, the carpule 14 being pushed into the holder 18 in the direction of the arrow 20 assuming the position illustrated in FIGS. 1 to 3. Here, the carpule 14 is fixed in position by catch elements 22 and stops 24 (FIG. 4) opposite the catch elements 22. The holder 18, which accommodates the preferably also circular cylindrical carpule 14 in the cylindrical opening 26, is connected with a cylindrical hub 28. The gas chamber 12 is formed within the cylindrical hub 28.

The gas chamber 12 is also sealed with a second piston 30. Optionally, the gas chamber may also be designed as a carpule. The also cylindrically shaped gas chamber 12 has a larger diameter than the active agent chamber 10. Of course, the arrangement of active agent and gas in the two chambers may also be inverted. This is particularly suitable with active agents that require only a little volume of gas for foaming, i.e. with active agent which are inherently easily foamed. The height of the gas chamber 12 and the active agent chamber 10 is substantially the same, the gas chamber 12 preferably being slightly higher to be able, if desired, to deplete both chambers 10, 12 entirely when the pistons 16, 30 are pushed in completely.

Connected to the second piston 30 is a connecting element 32 designed as a hollow needle. For this purpose, the piston 30 comprises a suitable, for example cylindrical hub 34 (FIG. 4) into which the hollow needle 32 may be inserted and retained, e.g., by gluing.

Further, a foam producing means 38 is rigidly or loosely and, if desired, removably connected to the piston 30 which sealingly abuts the inner wall 36 of the gas chamber 12. In particular, the foam producing means 38 comprises two sieves 40 that cause the whirling and mixing of the two media and thus the production of foam. The foam producing means 38 is connected to the piston 30 through a holder 42.

In addition to or instead of two or more sieves, the foam producing means 38 may also comprise, for example, one or more sinter filters, impellers, coils and/or spirals.

A loose or removable connection between the foam producing means 38 and the piston 30 is advantageous in that the foam producing means 38 can be pulled from the cylindrical hub 38 of the present device together with the syringe 46. When expelling the foam from the syringe 46, the foam is again pushed through the foam producing means 38 so that the quality of the foam produced can further be improved. Moreover, it is possible to provide the inner side of the cylindrical hub 29 with catch elements that prevent the piston 30 from being pulled from the cylindrical hub 28. Similarly, the piston 30 may comprise catch elements that, when the piston 30 is pulled too far out from the hub 28, engage in recesses, for example, provided in the hub 28.

The holder 42 has a foam exit opening 44 (FIG. 4) through which the foam produced in the foam producing means 38 escapes. In the particularly preferred embodiment of the invention illustrated, the foam exit opening is a Luer to which a conventional syringe 46 may be connected. The syringe 46 serves as a foam collecting receptacle, as is evident from FIGS. 2 and 3.

Figure 2:
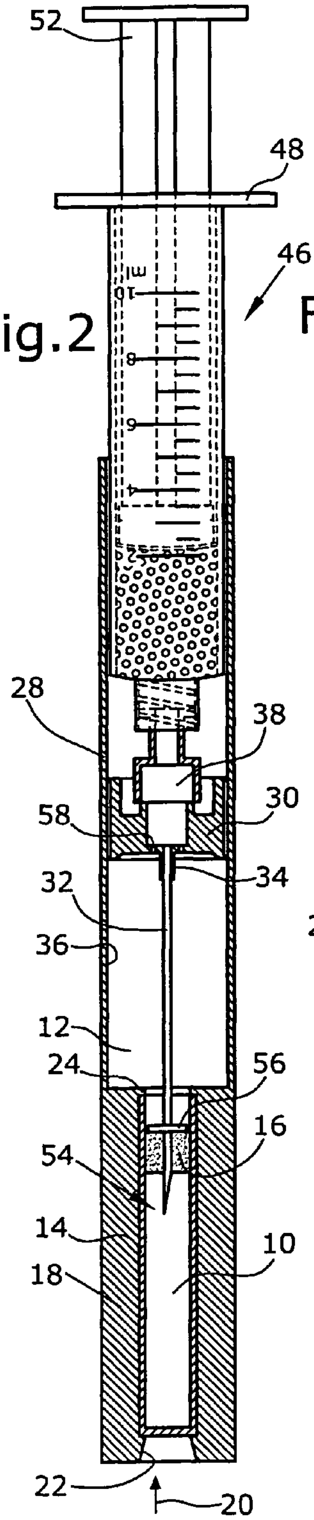
Figure 3:
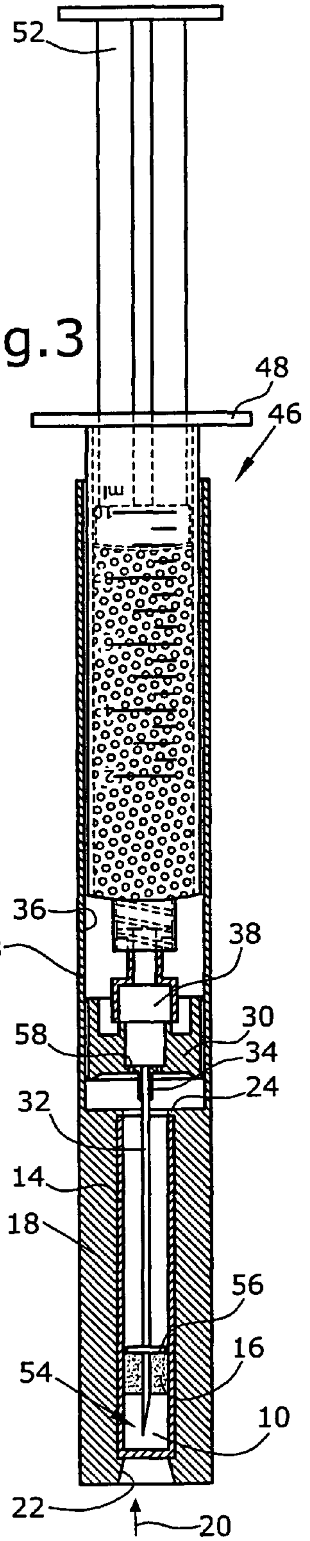
Figure 4:
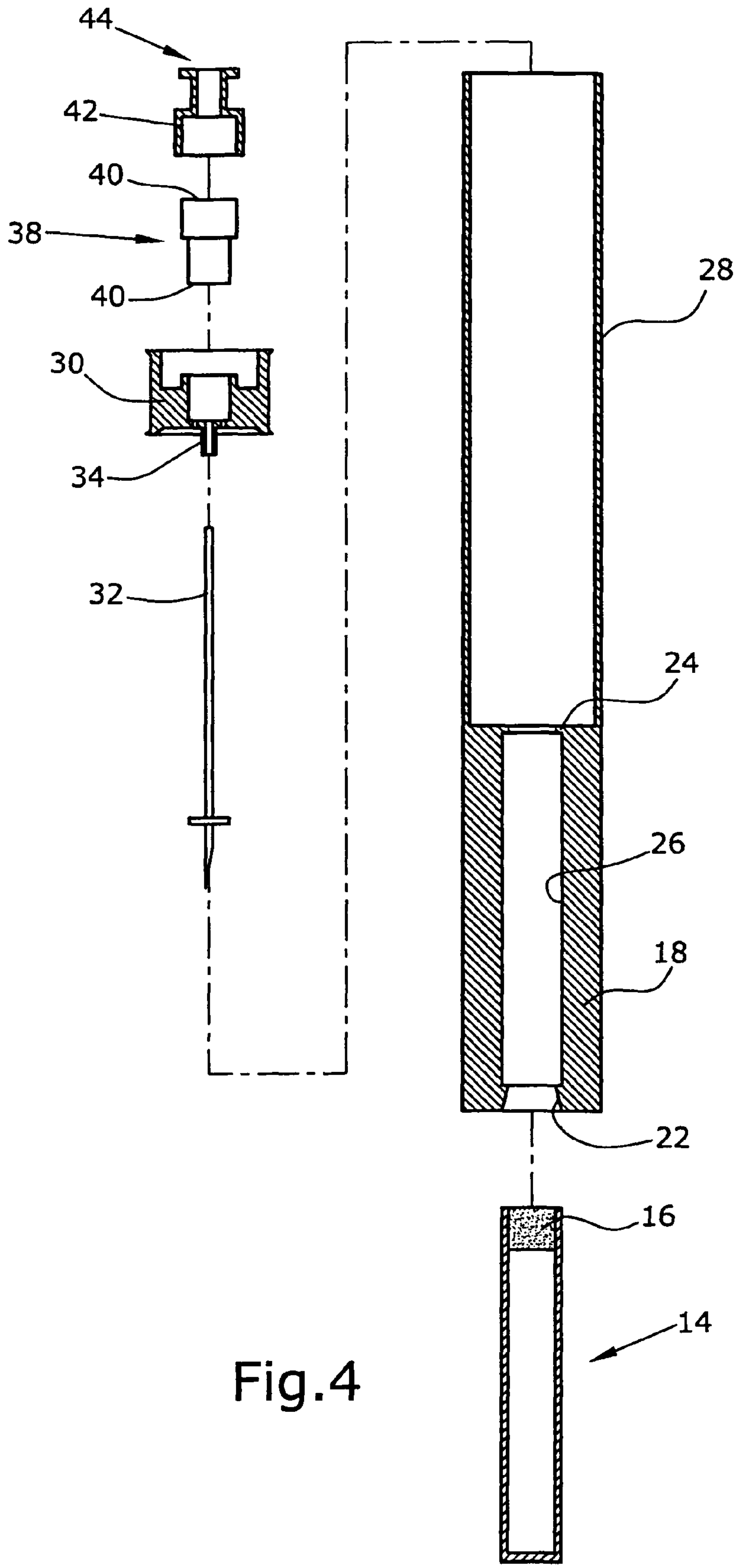

To produce foam, the holder 42 is placed on a substrate so that the device is orientated vertically, as illustrated in FIGS. 1-3. Thereafter, the syringe barrel is pushed downward in the direction of the arrow 50, for example using the hubs 48 illustrated in the Figures. The position of the syringe piston or syringe plunger 52 is not changed in the process. Shifting the syringe barrel downward into the holder 28, particularly shifts the foam producing means 38 as well as the second piston 30 downward. Together with the piston 30, the hollow needle 32 rigidly connected to the piston 30 is pushed downward. In doing so, the tip 54 of the hollow needle 32 pierces the first piston 16 and thus opens the active agent chamber 10.

Since an entrainment element 56, such as a plate, is rigidly connected to the connecting element or the hollow needle 32, the plate 56 presses the first piston 16 into the active agent chamber 10. The shifting of both pistons 30, 16 causes a pressure increase both in the active agent chamber (10) and in the gas chamber 12. Thereby, active agent is pressed through the hollow needle 32 into the foam producing means 38. Further, gas is pressed from the gas chamber 12 into the foam producing means 38 through openings 58 present in the piston 30 and/or through transverse bores in the hollow needle 32. Through the foam exit opening 44 of the foam producing means 38, the foam produced reaches the space 60 within the syringe barrel cleared by the movement of the syringe barrel.

It is an essential advantage of the present device that foam is produced in the syringe 46 by a single piston stroke, i.e. by pushing the two pistons 16, 30 down as illustrated in FIGS. 1-3. After the foam has been produced, the syringe may be removed from the Luer adapter so that the foam may then be applied directly.

What is claimed is:

1. A device for producing medicinal foam, comprising:

an active agent chamber closed with a first piston, a gas chamber closed with a second piston, the gas chamber and the active agent chamber being arranged one after another, and a foam producing device connected with the active agent chamber and the gas chamber, wherein the first and second pistons are interconnected and displaced in common to cause a pressure increase both in the active agent chamber and the gas chamber and to feed active agent and gas to the foam producing device, wherein the first and second pistons are interconnected through a connecting element which opens one of the active agent and gas chambers when it is displaced, wherein the first piston is displaced in the active agent chamber and the second piston is displaced in the gas chamber, and wherein the connecting element comprises a feed channel through which the active agent and/or gas can flow towards the foam producing device.

2. The device of claim 1, wherein the connecting element comprises an entrainment element for entraining one of the first and second pistons.

3. The device of claim 1, wherein the feed channel connects the active agent or gas chamber opened by the connecting element immediately with the foam producing device and/or the other of the active agent or gas chamber.

4. The device of claim 1, wherein the active agent and gas chambers adjoin each other.

5. The device of claim 1, wherein one of the first and second pistons is in particular rigidly connected to the foam producing device.

6. The device of claim 1, wherein the foam producing device has a foam exit opening connectable to a foam collecting vessel or an application aid.

7. The device of claim 1, wherein the foam producing device includes at least one sieve for producing foam.

8. The device of claim 1, wherein a slow-down element is provided that is arranged upstream of the foam producing device to cause a slowing of the active agent and thus a pre-mixing of the active agent and the gas.

9. The device of claim 1, wherein the connecting element has openings for the active agent and/or the gas to exit from the feed channel of the connecting element into a chamber.

10. A device for producing medicinal foam, comprising:

an active agent chamber closed with a first piston, a gas chamber closed with a second piston and closed with the first piston, a hollow needle connected to the second piston, the hollow needle having an open end directed towards the first piston, an entrainment element rigidly connected to the hollow needle offset from the open end, openings defined through the second piston and/or through transverse bores of the hollow needle, and a foam producing device connected with the hollow needle and the openings, wherein the hollow needle interconnects the first and second pistons in common to feed active agent through the hollow needle and gas through the openings to the foam producing device upon displacement of the hollow needle through the first piston to a point where the entrainment element contacts the first piston, wherein the foam producing device is connected to the second piston by a holder, and wherein the first piston is displaced in the active agent chamber and the second piston is displaced in the gas chamber.

11. The device of claim 10, wherein the foam producing device is removably connected to the second piston by a holder.

12. The device of claim 11, wherein the holder comprises a foam exit opening.

13. The device of claim 12, wherein the foam exit opening comprises a Luer to which a conventional syringe is connectable.

14. The device of claim 10, wherein the active agent chamber and the gas chamber are arranged one after another.

15. A device for producing medicinal foam, comprising:

an active agent carpule having a closed bottom end and an open top end;

a gas chamber having a bottom end and a top end;

a first piston closing the top end of the active agent carpule and the bottom end of the gas chamber;

a second piston closing the top end of the gas chamber;

a hollow needle between the first and second pistons, the hollow needle being connected to the second piston such that an open end of the hollow needle is directed towards the first piston;

a foam producing device connected to the second piston in fluid communication with the open end of the hollow needle and with the gas chamber; and an entrainment element rigidly connected to the hollow needle between the first and second pistons in a position offset from the open end of the hollow needle, wherein, upon displacement of the second piston to a point where the hollow needle pierces through the first piston and the entrainment element contacts the first piston, the entrainment element maintains a fixed distance between the first and second pistons to allow a pressure increase in both the active agent carpule and the gas chamber so that the active agent and the gas are fed to the foam producing means; and wherein the first piston is displaced in the active agent chamber and the second piston is displaced in the gas chamber.

16. The device of claim 15, further comprising at least one transverse bore in the hollow needle between the entrainment element and the second piston allowing fluid communication between the foam producing device and the gas chamber.

17. The device of claim 15, further comprising at least one opening in the second piston allowing fluid communication between the foam producing device and the gas chamber.

* * * * *